United States Patent
Van Der Meer

(10) Patent No.: US 6,763,591 B2
(45) Date of Patent: Jul. 20, 2004

(54) WATERTIGHT HOUSING OF AN APPARATUS

(75) Inventor: Mattheus Jacobus Van Der Meer, Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 57 days.

(21) Appl. No.: 10/144,832

(22) Filed: Oct. 25, 2001

(65) Prior Publication Data

US 2002/0184769 A1 Dec. 12, 2002

(30) Foreign Application Priority Data

Nov. 2, 2000 (EP) .............................................. 00203830

(51) Int. Cl.[7] .............................................. B26B 19/35
(52) U.S. Cl. ...................... 30/43.6; 30/DIG. 1; 429/82; 429/89
(58) Field of Search .............................. 30/43.92, 43.6, 30/43.5, DIG. 1; 429/82, 89

(56) References Cited

U.S. PATENT DOCUMENTS 4,052,534 A * 10/1977 Devitt .......................... 429/86
6,348,281 B1 * 2/2002 Li ................................ 429/53
2001/0023538 A1 * 9/2001 Muraguchi et al. ......... 30/43.92

FOREIGN PATENT DOCUMENTS

| EP | 0262070 A1 | 3/1988 | ............ H01M/2/12 |
| FR | 2551172 A1 | 3/1985 | ......... F16K/31/126 |
| WO | 96/08048 | 3/1996 | |

* cited by examiner

Primary Examiner—Douglas D. Watts
(74) Attorney, Agent, or Firm—Ernestine C. Bartlett

(57) ABSTRACT

The invention relates to a waterproof housing (1) of an apparatus, for example an electrically rechargeable shaving device, which housing (1) is provided with at least one opening (3a,3b) in a wall (1a), which opening is sealed off by means of a foil (4) permitting the equalization of a pressure difference between the inside of the housing and the outer atmosphere.

In order to provide means for the equalization of a pressure difference suitable for all kinds of apparatuses, which means are not susceptible of contamination and at the same time are capable of equalizing pressure differences, the foil (4) is elastically deformable and provided with at least one incision (8,9) of which the cutting edges can yield owing to a pressure difference across said foil.

8 Claims, 3 Drawing Sheets

WATERTIGHT HOUSING OF AN APPARATUS

The invention relates to a watertight housing of an apparatus, for example an electrically chargeable shaver, which housing is provided with at least one opening in a wall, which opening is closed off by a foil, said foil rendering possible a pressure equalization in the housing with respect to the outer atmosphere.

The invention further relates to a watertight housing of an apparatus, for example an electrically chargeable shaver, wherein in the housing a separate battery compartment is present for accommodating rechargeable cells or batteries, which battery compartment is provided with at least one opening in a wall, which opening is closed off by a foil which renders possible the escape of gases generated during charging of the batteries from the battery compartment to the outer atmosphere.

The invention further relates to a battery compartment for accommodating rechargeable cells or batteries, for example for use in an apparatus, for example an electrically chargeable shaver, which compartment is provided with at least one opening in a wall, which opening is closed off by a foil which renders possible the escape of gases generated during charging of the batteries from the battery compartment to the outer atmosphere.

Since various devices, for example electrically chargeable shavers, electric toothbrushes and the like are used in humid rooms, such as a bathroom, such devices should be at least splash-proof for reasons of safety. Seals have been provided for this purpose in the housing in suitable locations, for example on the connection seams of the various housing parts or at the areas of certain components such as shaver heads, switches, collectors, etc.

A pressure difference may arise between the interior of the housing and the outer atmosphere owing to temperature differences, for example owing to cleaning of such an apparatus under a hot tap. The resulting pressure difference may damage the seals mentioned above, so that the apparatus is no longer watertight, which is undesirable in view of the safety risks.

To equalize such pressure differences without damage to the seals in a simple and most of all fast manner, one or several openings are provided in the housings of present-day devices of the type mentioned above, which openings are screened off by a gas-transmitting foil, for example of the watertight Gore-Tex® type. The term foil denotes a flexible layer of any material such as, for example, rubber or synthetic resin.

Such watertight, gas-transmitting foils are also used in battery compartments which are present in the housings of electrically chargeable devices. An example of such an application is disclosed in the international patent application No. PCT/US 95/01054 published under No. WO 96/08048.

In such an application, the foil serves to provide a possibility for gases to escape, in particular explosive hydrogen gas $H_2$ which is generated during charging of the batteries at the area of the positive electrode and accordingly creates an undesirable overpressure in the battery compartment.

Next to the fact that such materials are comparatively expensive, such "breathing" foils are highly sensitive to pollution, owing to which the gas-transmitting pores of the foil are choked up in the course of time, and the foil accordingly loses its "breathing" function. In addition, such foils transmit gas in one direction only, which limits their pressure equalization function.

The invention has for its object to provide a pressure equalization means for use in apparatuses of the kind mentioned above which are not only insensitive to pollution but are also capable of equalizing a plurality of pressure differences.

To achieve this object, the foil is elastically deformable and provided with at least one continuous incision whose cutting edges can yield under the influence of a pressure difference obtaining across the foil. Since the opening in the foil does not open until a pressure difference is present, it cannot become contaminated and choked up during normal use.

In addition, pressure equalization can now take place in two directions with such a mechanically deformable foil. Both an overpressure and an underpressure can be equalized with respect to the outer atmosphere, which is highly desirable in view of the service life of the apparatus and which cannot be achieved by foils which equalize pressures in one direction only.

The pressure at which the incision in the foil opens can be influenced by the choice of a mechanically deformable foil. This opening pressure is influenced not only by the material properties of the foil, but constructional properties also play a part. Since the operational surface areas of the foil in the region of the opening are mutually unequal in an embodiment of the invention, the required opening pressure for an overpressure may be different from the required opening pressure for an underpressure in the housing or battery compartment, and may in addition be adjustable.

In more specific embodiments according to the invention, the incision in the foil may be a straight or a curved incision.

The invention will now be explained in more detail with reference to a drawing, in which.

Figure 1:
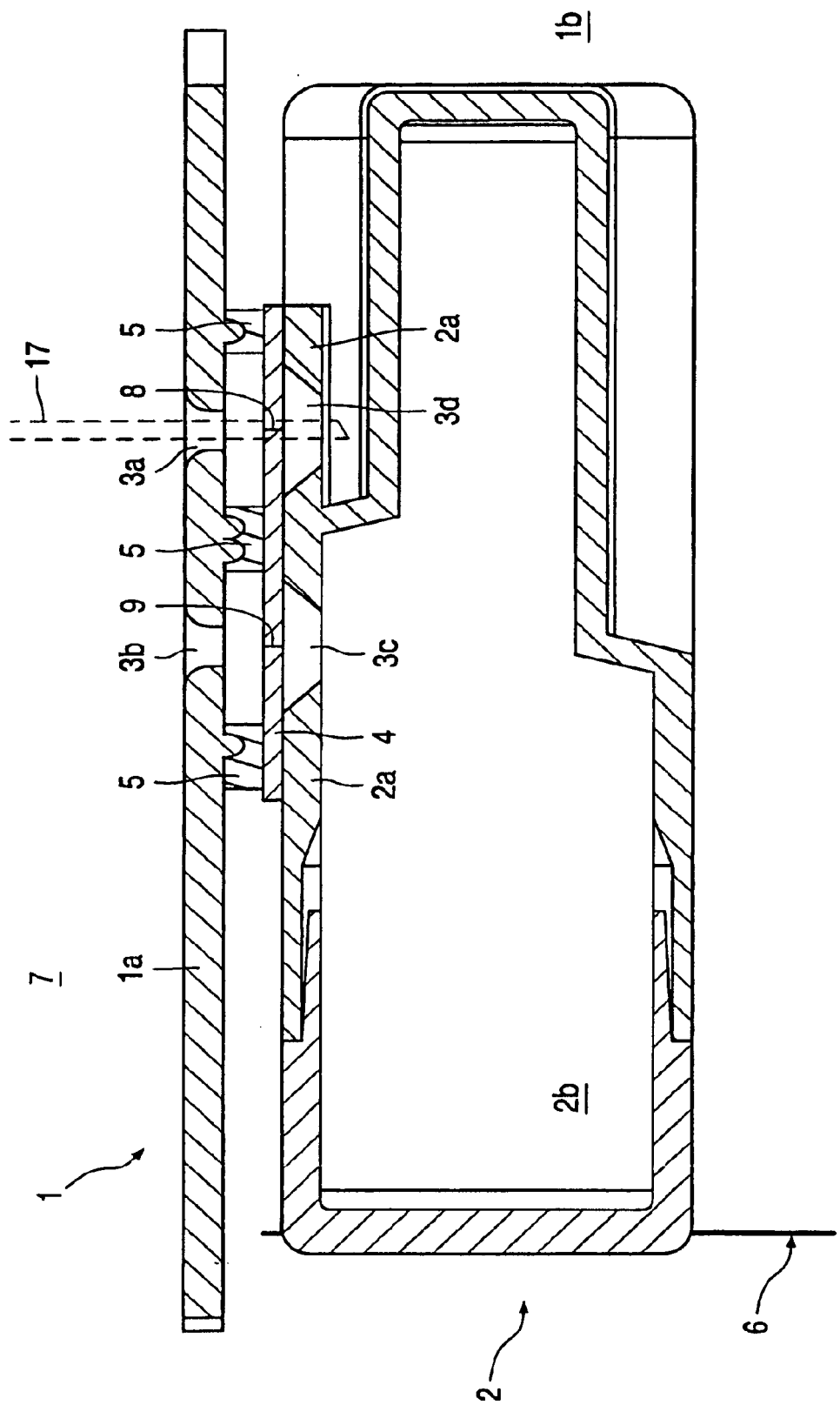
FIG. 1 shows a housing and a battery compartment of an apparatus provided with an embodiment of pressure equalization means according to the invention.

FIG. 1 diagrammatically shows a partial cross-section through a housing of an electrically chargeable apparatus. The housing 1 is formed by a wall 1a and is preferably made from a synthetic resin.

An electrically chargeable apparatus, such as a shaver, an electric toothbrush and the like, is often used in a humid room, such as a bathroom. The housing of the apparatus should be at least splash-proof for reasons of safety, and seals are made in suitable locations in the housing for this purpose.

Pressure differences will arise between the interior 1b of the housing 1 and the outer atmosphere 7 owing to temperature differences, for example caused by cleaning of such an apparatus under a hot tap. These pressure differences may damage the seals, with the result that the relevant apparatus is no longer watertight.

An opening 3a is provided in the wall 1a of the housing 1 for a fast equalization of such a pressure difference, which opening is in communication with the interior 1b of the housing 1. To prevent moisture and other impurities from entering the housing 1 through the opening 3a, said opening 3a is closed off by means of a foil 4 which is enclosed between support means 5 and a wall portion 2b which in this embodiment forms part of the battery compartment 2. The wall portion 2b is also provided with an opening 3d here. It will be obvious that the opening 3a may alternatively be provided in a different place in the wall 1a of the housing, and that the foil 4 may be clamped in in an alternative, known manner at the area of this opening 3a, thus screening off the opening 3a from the interior 1b of the housing 1.

According to the invention, the foil is manufactured from an elastically deformable material, for example rubber or some other synthetic resin material, and is in addition provided with a continuous incision 8. A gas pressure difference arising across the foil 4 (between the opening 3a with atmospheric pressure 7 and the opening 3d connecting to the interior 1b of the housing 1) will deform the foil 4 at the area of the incision 8. As a result, the two cutting edges 8a and 8b (see FIG. 2b) will move away from one another, so that the pressure difference can be equalized owing to the opening which has arisen in the foil.

The use of an elastically deformable foil 4 provided with an incision 8 renders it possible to equalize both an overpressure and an underpressure prevailing in the housing 1 with respect to the outer atmosphere 7. In the case of an overpressure, the two cutting edges 8a and 8b will yield in a direction towards the opening 3a in the wall 1a, whereas the cutting edges will yield towards the interior 1b of the housing 1 in the case of an underpressure with respect to the outer atmosphere 7; see FIG. 2b.

This pressure equalization acting in two directions renders the pressure equalization means according to the invention highly suitable for use in many kinds of apparatuses, such as an electrically chargeable shaver, or an electric iron, or an electric toothbrush.

Since the incision 8 does not open until a pressure difference is present, it cannot become contaminated or choked up when not in use, in contrast to the gas-transmitting foils.

A similar embodiment of the pressure equalization means according to the invention is used in the battery compartment 2 also shown in FIG. 1 and accommodated in the housing 1. The separate battery compartment 2 is fastened to the inside of the wall 1a by support means 5. Rechargeable cells or batteries (not shown) are accommodated in the battery compartment and can be charged through contacts 6 to provide the electric drive for the apparatus.

During charging of the cells or batteries, gases are evolved at the area of the positive electrode, in particular explosive hydrogen gas $H_2$, which gases will accumulate in the battery compartment 2 and thus generate an overpressure with respect to the outer atmosphere 7. Such an overpressure is highly undesirable, not only on account of the explosive character of the gases, but also on account of the risk of damage to the essential seals of the battery compartment 2 and the housing 1.

To allow such gases to escape from the battery compartment 2 to the outer atmosphere 7, openings 3c and 3b are provided in the wall 2a of the battery compartment and in the wall 1a of the housing, respectively. The opening 3c provided in the battery compartment is closed off by the same foil 4 which also serves for screening off the opening 3a in the wall 1a of the housing 1. The foil 4 here lies enclosed between the wall 2a of the battery compartment and the support means 5.

The foil 4 is provided with an incision 9 at the area of the opening 3c again, the cutting edges 9a and 9b thereof yielding under the influence of an overpressure generated in the battery compartment 2. Gases evolved during charging of the batteries can escape from the battery compartment 2 as a result of this; see also FIG. 2a.

Figure 2A:
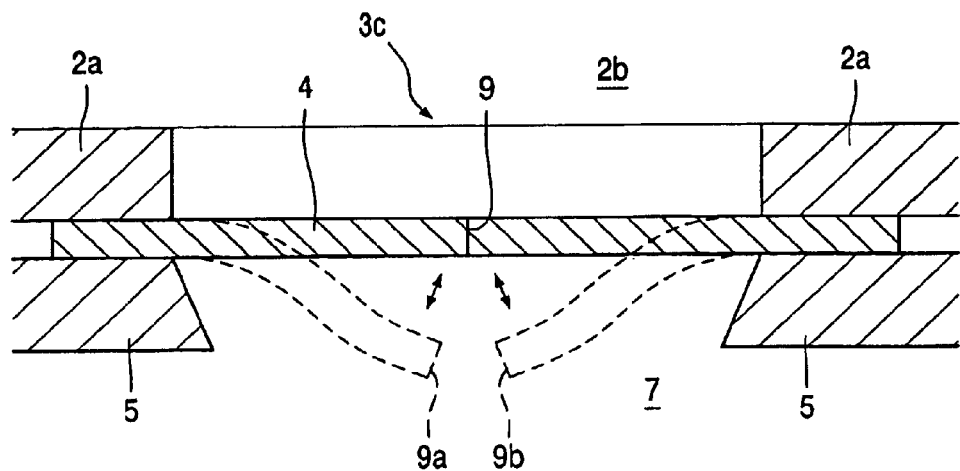
FIGS. 2a and 2b are diagrammatic partial elevations of details of the pressure equalization means of FIG. 1.
Figure 2B:
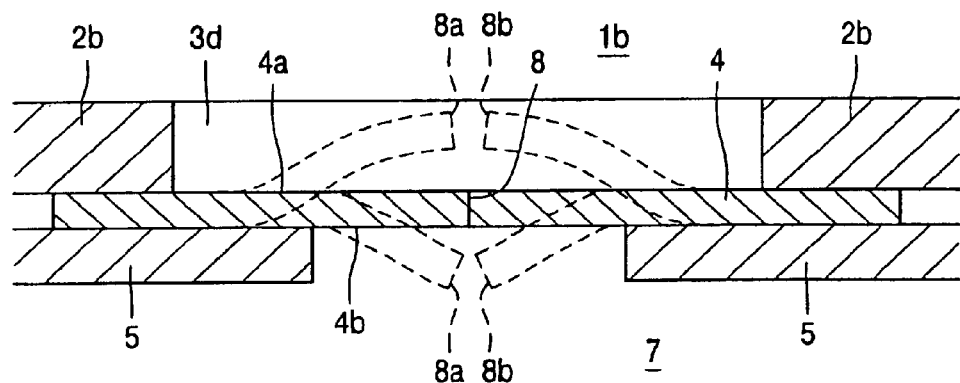

FIGS. 2a and 2b are two partial views of the foil 4 at the area of an opening on an enlarged scale. The foil 4 is clamped in between two plate parts of which one plate part forms the wall 2a of the battery compartment 2 in FIG. 2a and the other plate part the support means 5. The foil 4 screens the interior 2b of the battery compartment 2 off from the outer atmosphere 7. The incision 9 provided in the foil 4 has a number of cutting edges 9a and 9b which can move away from one another under the influence of a pressure difference obtaining across the foil 4, as is indicated with broken lines. In FIG. 2a, an overpressure is present in the interior 2b of the battery compartment 2, for example caused by gases evolved during charging of the batteries.

Since the foil is mechanically deformed under the influence of a gas pressure difference, it is possible to influence the gas pressure at which the incision 9 in the foil 4 opens. The minimum overpressure or underpressure at which the incision is pressed apart can be influenced in that the foil 4 is made thicker or in that a foil material of greater or smaller elasticity is used as the pressure equalization means.

An effective constructional measure whereby the incision is forced open at different overpressure and underpressure is shown in FIG. 2b. Here the foil 4 is clamped in between a projecting wall portion 2b (of the battery compartment, cf. FIG. 1) and the support means 5. The foil 4 screens the interior 1b of the housing 1 off from the outer atmosphere 7.

As FIG. 2b shows, the effective surface areas of the foil in the region of the opening are mutually unequal. The effective foil surface area 4a at the housing side 1b is larger than the effective foil surface area 4b at the outer atmosphere side 7. The plate part 5 rests against a larger foil surface area at the side 4b than at the other side. In contrast to FIG. 2a, the mechanical elastic deformation of the foil 4 at an overpressure in the interior 1b will differ from the mechanical elastic deformation of the foil at an underpressure in the interior 1b. The overpressure necessary for opening the incision 5 towards the outer atmosphere 7 will be higher, because of the counterpressure of the plate part 5 which may be expected, than the underpressure required for opening the incision towards the interior 1b.

Figure 3A:
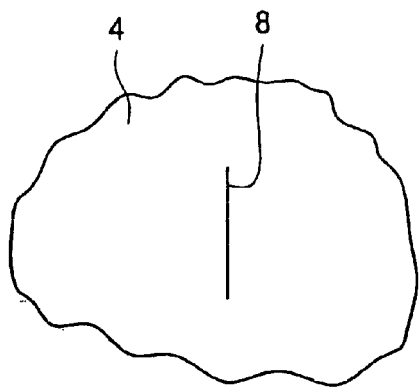
FIGS. 3a and 3b are further diagrammatic partial elevations of embodiments of pressure equalization means according to the invention.
Figure 3B:
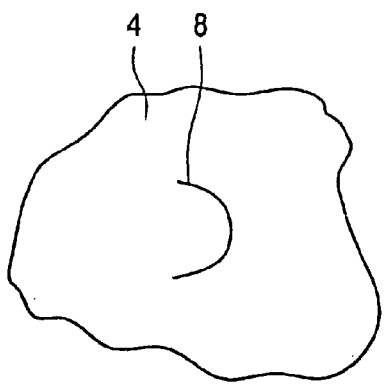

FIGS. 3a and 3b show two embodiments of the shape of the incisions 8 in the foil material. This may be a straight shape (FIG. 3a) or a curved shape (FIG. 3b). An incision with a V-shape is also very suitable. The curved shape may be provided, for example, by means of a hypodermic needle.

Furthermore, it is possible to carry out an overpressure or underpressure test in the space 1b or 2b of the housing 1 or the battery compartment 2, respectively, shielded by the foil in that a hypodermic needle 17 (see FIG. 1) is passed through the foil 4. Information may be obtained on whether the foil is impermeable to gases or liquids by such a method. After the hypodermic needle has been removed, the foil closes again substantially hermetically, in spite of the incision 8 or 9 provided, and surprisingly does not even allow water to pass and is also capable of withstanding a comparatively great pressure difference.

Figure 4:
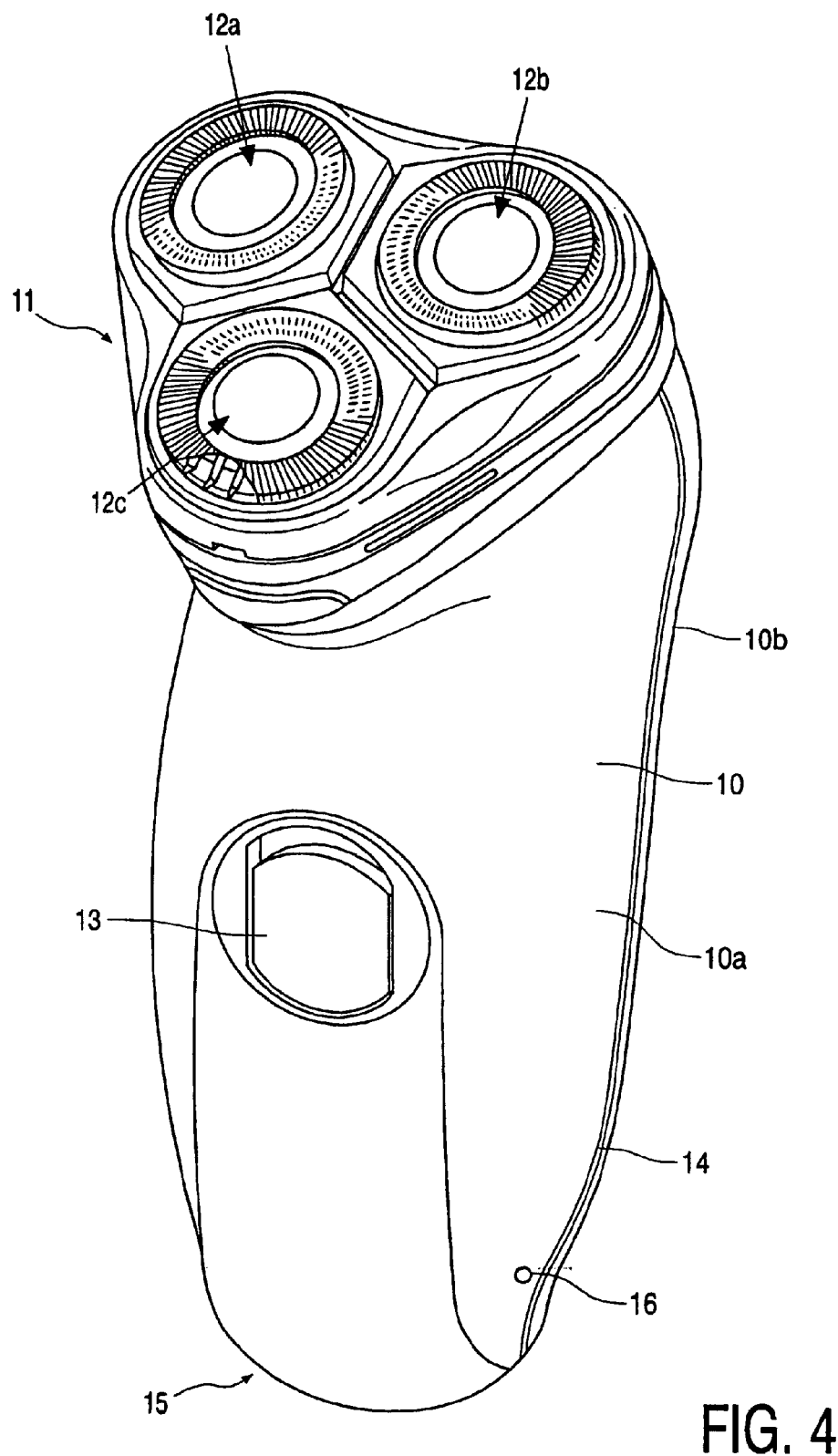
FIG. 4 shows an electrically chargeable shaver provided with pressure equalization means according to the invention.

FIG. 4 shows an electrically chargeable shaver as an example of an application, provided with pressure equalization means according to the invention. The electric shaver consists of a housing 10 and a shaver head 11 provided with three cutter assemblies 12a–12c. The shaver is also provided with a switch 13 for switching the apparatus on or off. The housing 10 is formed by a number of housing parts 10a and 10b which are interconnected by means of a watertight (i.e. splash-proof) seal 14 in view of the use of the apparatus in an often humid space.

The housing may accommodate, for example, a battery compartment (not shown), such that the batteries held in this compartment can be electrically charged via the connector 15. An opening 16 is provided in the housing 10 for solving the above problem of pressure equalization between the housing and/or the battery compartment on the one hand and the outer atmosphere on the other hand, which opening is screened off by a foil 4 according to the invention (see FIGS. 1 to 3).

What is claimed is:

1. A watertight housing of an apparatus, said housing having a wall with at least one opening, which opening is closed off by a foil, said foil rendering possible a pressure equalization in the housing with respect to the outer atmosphere, characterized in that said foil is elastically deformable and provided with at least one continuous curved incision having cutting edges which yield under the influence of a pressure difference obtaining across the foil, said foil preventing passage of liquids through said opening unless there is a pressure difference between two sides of the foil.

2. A watertight housing as claimed in claim 1, characterized in that the operational surface areas of the foil in the region of the opening are mutually unequal.

3. A watertight housing of an apparatus, wherein in the housing a separate battery compartment is present for accommodating rechargeable voltaic cells or batteries, which battery compartment is provided with at least one opening in a wall, which opening is closed off by a foil which renders possible the escape of gases generated during charging of the batteries from the battery compartment to the outer atmosphere, characterized in that said foil is elastically deformable and provided with at least one continuous incision having cutting edges which yield under the influence of a pressure difference obtaining across the foil, said foil preventing passage of gases through said opening unless there is a pressure difference between two sides of the foil.

4. A watertight housing as claimed in claim 3, characterized in that the operational surface areas of the foil in the region of the opening are mutually unequal.

5. A watertight housing as claimed in claim 3, characterized in that the incision is a straight incision.

6. A watertight housing as claimed in claim 3, characterized in that the incision is a curved incision.

7. An apparatus provided with a watertight housing or a battery compartment as claimed in claim 1.

8. A method of measuring a gas pressure in a watertight housing or a battery compartment of an apparatus, for example an electrically chargeable shaver, for the purpose of testing the sealing of the apparatus, which housing or battery compartment is provided with at least one opening in a wall, which opening is sealed off by a foil, said foil forming a pressure equalization means which renders possible a pressure equalization in the housing with respect to the outer atmosphere, characterized in that said foil is elastically deformable and provided with at least one continuous incision having cutting edges which yield under the influence of a pressure difference obtaining across the foil, said foil preventing passage of liquids through said opening unless there is a pressure difference between two sides of the foil, and the method comprises passing a hypodermic needle through the foil, which needle is coupled to a gas pressure measuring device.

* * * * *